United States Patent
Hirochika et al.

(10) Patent No.: US 7,034,139 B2
(45) Date of Patent: Apr. 25, 2006

(54) RICE GENE FOR CONTROLLING TOLERANCE TO SALT STRESS

(75) Inventors: Hirohiko Hirochika, Tsukuba (JP); Akio Miyao, Tsukuba (JP); Shin Takeda, Saitama (JP); Kiyomi Abe, Saitama (JP)

(73) Assignees: Incorporated Administrative Agency, (JP); National Agriculture and Bio-Oriented Research Organization, (JP)

( * ) Notice: Subject to any disclaimer, the term of this patent is extended or adjusted under 35 U.S.C. 154(b) by 316 days.

(21) Appl. No.: 10/344,980

(22) PCT Filed: Aug. 6, 2002

(86) PCT No.: PCT/JP02/08041

§ 371 (c)(1),
(2), (4) Date: May 16, 2003

(87) PCT Pub. No.: WO01/30990

PCT Pub. Date: May 3, 2001

(65) Prior Publication Data

US 2004/0016027 A1    Jan. 22, 2004

(30) Foreign Application Priority Data

Aug. 7, 2001   (JP) .............................. 2001-239980

(51) Int. Cl.
*C12N 15/29* (2006.01)
*C07H 21/04* (2006.01)

(52) U.S. Cl. .................................... 536/23.6
(58) Field of Classification Search .............. 536/23.1, 536/23.6; 800/295, 278; 435/419, 468
See application file for complete search history.

(56) References Cited

FOREIGN PATENT DOCUMENTS

WO       WO 0130990        5/2001

OTHER PUBLICATIONS

Moons et al. 1997. Planta. vol. 202. pp. 443-454.*
Guo et al. 2004. PNAS. USA. vol. 101. pp. 9205-9210.*
Lazar et al. 1988. Molecular Biology of the Cell. vol. 8. pp. 1247-1252.*
Hill et al. 1998. Biochem & Biophysics Res Comm. vol. 244. pp. 573-577.*
Igrashi et al. 1997. Plant Mol Biol. vol. 33. pp. 857-865.*
Igarashi et al., *Characterization of the gene for $\Delta^1$-pyrroline-5-carboxylate synthetase and correlation between the expression of the gene and salt tolerance in Oryza sativa L*, published by Kluwer Academic Publishers in *Plant Molecular Biology*, 33, pp. 857-865, 1997.
Hoshida et al., *Enhanced tolerance to salt stress in transgenic rice that overexpressses chloroplast glutamine synthetase*, published by Kluwer Academic Publishers in *Plant Molecular Biology*, 43, pp. 103-111, 2000.

* cited by examiner

*Primary Examiner*—Ashwin Mehta
(74) *Attorney, Agent, or Firm*—Fay, Sharpe, Fagan, Minnich & McKee, LLP

(57) ABSTRACT

A gene encoding a protein capable of controlling salt stress tolerance is provided. A polynucleotide encoding a plant gene capable of controlling salt stress tolerance is provided. The polynucleotide includes a polynucleotide which has a nucleotide sequence encoding an amino acid sequence from methionine at position 1 to asparagine at position 243 of SEQ ID NO: 2 in the sequence listing, or which has a nucleotide sequence encoding the amino acid sequence having one or several amino acid deletions, substitutions and/or additions and is capable of controlling salt stress tolerance.

6 Claims, 6 Drawing Sheets

FIG. 3

```
   1  AAAATTTCCC CTTTCCTCTC CACGCCAAGA AACGCAAAAC
  41  CCCCACGCCG ACCAAGGCGA GAAGCGCCGC CGCCGAATCG
  81  AACCGCGATC GCGCCCTTCT CCCGCCGCCC CCGCGCGCTC
 121  TTCTCCTCCT CGTCCTCGAC GCCGCTGTGC CGGAGTTTAG
 161  GCGGAGATCG ATCCGGAGCG GGGTTTCTCT TCTACCTGGC
 201  AAGGTTGAGG AAGAAAAGCT TGCTGATTTG TGATGGCTGC
 241  CCCAACTGCA ACAGCTGTTT TTCTTGATGA GAACCTGCAT
 281  ATCCATAGGG GGCCTGCTGG CAAGAGGGCT GATGGATTGA
 321  AGGCCAAGCC ACTGAAGCCA TTAGCAGCAA AGCAAGGGCT
 361  TCAAGAGAAG AAGGCCCTGA GGGATGTATC CAACATTGGC
 401  AAGCCCCGG TGTCTACGCG GAAGCCCCTG CAGGACGTGT
 441  CCAACACCGC CAAGCCCCGA GGGCGCAACA TTTCTGATGG
 481  CACTACCTTG AAGAAGACTG CTCTTCGCAG CCATGAGGCC
 521  ACCAAGAACC CAGTGAAGAA GACTGTAATC TTTTCTGATG
 561  AGACCGCAAA ATGTCATGAA TGGGCTAAGG ATGGGGTGGA
 601  GGGCACCCAC TTCACTGGGA ATGATTCTCA GAAGTTGGAA
 641  AAGGACAGTC AAGACAAACG TGTCAAGAAG AAGGTGGAGA
 681  AAATAATGTC AGCATTGCAC GACTGGCCAG ACGCGGTATT
 721  TGATCATGTG CTTTTTCCAT CTGAGGTGGT AGCAGCGTTT
 761  TTTGAAGAAG TAAAAGAGAT GGAGCTGGAA CCTGAGATTC
 801  TTCCAGAGAA CAATAGGCGT CGCTCAAGTT CAGGTGATAA
 841  AATGAAGCTG GCTGAAGATC CTTTCACGGA AGACGAGCTT
 881  GACTACTACC CATTTCTTGA GAACAATCCC GTTGAGTTTC
 921  AGCTGAGAGA TGAGCTACCA CTCCTGGAGC CTGGAATGAA
 961  CTGAAGAATG CTAATCTGCC CCACTTGAAA AGACCTCAGA
1001  ACAGTGCTAT TATCATCATT ATCCTCTTTG CAAACTCTAC
1041  TTGCTCAGGA GCAGTTTATT TGTAGTAGTA GTAGTAGTAA
1081  CTAGTATCCT AGATGTTCTG CTGTATGTGG TTGGTGTGAT
1121  AATCATTCAC ACTTTAGGAA GAACCCAAGT AGCG
```

FIG. 4

|  | 10 | 20 | 30 | 40 | 50 |
|---|---|---|---|---|---|
|  | MAAPTATAVF | LDENLHIHRG | PACKRADCLK | AKPLKPLAAK | QGLQEKKALR |
|  | 60 | 70 | 80 | 90 | 100 |
|  | DVSNIGKPPV | STRKPLQDVS | NTAKPRGRNI | SDGTTLKKTA | LRSHEATKNP |
|  | 110 | 120 | 130 | 140 | 150 |
|  | VKKTVIFSDE | TAKCHEWAKD | GVEGTHFTGN | DSQKLEXDSQ | DKRVKKKVEK |
|  | 160 | 170 | 180 | 190 | 200 |
|  | IMSALHDWPD | AVFDHVLFPS | EVVAAFFEEV | KEMELEPEIL | PENNRRRSSS |
|  | 210 | 220 | 230 | 240 |  |
|  | GDKMKLAEDP | FTEDELDYYP | FLENNPVEFQ | LRDELPLLEP | GMN* |

RICE GENE FOR CONTROLLING TOLERANCE TO SALT STRESS

TECHNICAL FIELD

The present invention relates to a novel gene. More particularly, the present invention relates to a novel gene encoding a protein having a function of controlling salt stress tolerance in plants.

BACKGROUND ART

Plants constantly suffer from stresses even in a normal growth environment. Such stresses variously include salt, drying, high temperature, low temperature, intense light, air pollution, and the like. Salt stress has received attention in terms of agricultural production. When soils and stones are decomposed, salts are generated, and the generation of salts is constantly continued. When it rains, the salts may flow into the river or the sea. In desert areas of low rainfall, a lesser amount of salts flow out, so that the salt concentration is considerably higher in soil water. Plants draw salts (nutrients) along with water osmotically through roots. When the salt concentration is high, plants cannot draw water. Moreover, the growth of the plants is inhibited due to physiological actions specific to ions. It is known that responses of plants to a salt stress overlap responses to environmental stresses, such as drying, high osmotic pressure, low temperature, and the like. These stresses lead to considerably severe damage to agriculture.

Recently, due to use of fertilizers in bulk or long-term sequential cropping, it is often observed that a high concentration of salt is accumulated in soil. Especially in greenhouse soil, detrimental salt accumulation frequently occurs. In areas near seashores, sea water or sea breeze causes damage. In arid or semiarid regions, salts are accumulated in the surface layer of soil due to excessive evaporation. These problems limit use of agricultural lands. In order to solve such problems, generally, the affected soil is exchanged or salts are removed by irrigation. However, these methods require huge expense or effort. The removal of salts by irrigation causes a large volume of salt water to flow into surrounding regions, leading to environmental pollution. Restriction of irrigation is now under consideration.

Therefore, it is very important to find a plant tolerant to such a salt stress.

According to studies for salt tolerant plants, which have been carried out at home and abroad, it is known that when salt tolerant plants are transferred from under non-stress conditions to salt stress conditions, expression of new genes is induced and the products of these genes play a role in salt stress tolerance. It is known that among plants of the genus Nicotiana, there are some types of plant having salt stress tolerance. Isolation of a relevant gene has been reported (Nelson et al., (1992) Plant Molecular Biology, vol. 19, 577–588; Yun et al. (1996) Plant Physiology, vol. 111, 1219–1225). Another exemplary gene of plants of the genus Nicotiana relating to response to a salt stress is a gene derived from *Nicotiana paniculata* of a type having salt stress tolerance, which is described in Japanese Laid-Open Publication No. 11-187877, Japanese Laid-Open Publication No. 11-187878, Japanese Laid-Open Publication No. 11-187879, and Japanese Laid-Open Publication No. 11-187880. Japanese Laid-Open Publication No. 11-187877 describes a novel gene induced by salt stress. A gene product encoded by this gene is considered to have a function of conferring moisture stress tolerance to plants. Japanese Laid-Open Publication No. 11-187878 describes a novel potassium channel gene induced by salt stress. The potassium channel gene encoded by this gene is considered to have a function of conferring moisture stress tolerance to plants. Japanese Laid-Open Publication No. 11-187879 describes a novel INPS gene induced by salt stress. The INPS gene encoded by this gene has a function of conferring moisture stress tolerance to plants. Japanese Laid-Open Publication No. 11-187880 describes a novel chloroplast type fructose bisphosphate aldolase induced by salt stress. The aldolase encoded by this gene is considered to have a function of conferring moisture stress tolerance to plants.

Two genes relating to response to salt stress in rice are chloroplast glutamine synthetic enzyme (GS2) gene (Hoshida et al., Plant Mol. Biol. 43:103–11(2000)); and Δ1-pyrroline-5-carboxylate (P5C) synthetic enzyme (OsP5CS) gene (Igarashi et al., Plant Mol. Biol. 33:857–65 (1997)). In the above-mentioned literature, it is described that the GS2 gene enhances photorespiration ability so that salt stress tolerance is conferred to a plant. A gene for OsP5CS involved in biosynthesis of proline is induced by a high concentration of salt, dehydration, abscisic acid treatment, and low temperature. Expression of the OsP5CS gene under salt stress is stably increased in a salt tolerant cultivar Dee-gee-woo-gen, while it is slightly increased in salt sensitive bred variety IR28.

A number of gene disruption strains of rice have been produced by the property of rice retrotransposon Tos17 that it is activated by culture to undergo transposition. Transposons are mutagenic genes which are ubiquitous in the genomes of animals, yeast, bacteria, and plants. Transposons are classified into two categories according to their transposition mechanism. Transposons of class II undergo transposition in the form of DNA without replication. Examples of class II transposons include Ac/Ds, Spm/dSpm and Mu elements of maize (*Zea mays*) (Fedoroff, 1989, Cell 56, 181–191; Fedoroff et al., 1983, Cell 35, 235–242; Schiefelbein et al., 1985, Proc. Natl. Acad. Sci. USA 82, 4783–4787), and Tam element of Antirrhinum (*Antirrhinum majus*) (Bonas et al., 1984, EMBO J, 3, 1015–1019). Class II transposons are widely used for gene isolation by means of transposon tagging. Such a technique utilizes a property of transposons, that is, a transposon transposes within a genome and enters a certain gene and, as a result, such a gene is physiologically and morphologically modified, whereby the phenotype controlled by the gene is changed. If such a phenotype change can be detected, the affected gene may be isolated (Bancroft et al., 1993, The Plant Cell, 5, 631–638; Colasanti et al., 1998, Cell, 93, 593–603; Gray et al., 1997, Cell, 89, 25–31; Keddie et al., 1998, The Plant Cell, 10, 877–887; and Whitham et al., 1994, Cell, 78, 1101–1115).

Transposons of class I are also called retrotransposons. Retrotransposons undergo replicative transposition through RNA as an intermediate. A class I transposon was originally identified and characterized in Drosophila and yeast. A recent study has revealed that retrotransposons are ubiquitous and dominant in plant genomes (Bennetzen, 1996, Trends Microbiolo., 4, 347–353; Voytas, 1996, Science, 274, 737–738). It appears that most retrotransposons are an integratable but non-transposable unit. Recently, it has been reported that some retrotransposons of such a type are activated under stress conditions, such as injury, pathogen attack, and cell culture (Grandbastien, 1998, Trends in Plant Science, 3, 181–187; Wessler, 1996, Curr. Biol., 6, 959–961; Wessler et al., 1995, Curr. Opin. Genet. Devel., 5, 814–821). For example, such activation under stress conditions was found in retrotransposons of tobacco, Tnt1A and Tto1 (Pouteau et al., 1994, Plant J., 5, 535–542; Takeda et al., 1988, Plant Mol. Biol., 36, 365–376), and a retrotransposon of rice, Tos17 (Hirochika et al., 1996, Proc. Natl. Acad. Sci. USA, 93, 7783–7788).

The rice retrotransposon Tos17 is a class I element in plants which has been extensively studied. Tos17 was cloned by RT-PCR using degenerate primers which had been prepared based on a conserved amino acid sequence of the reverse transcriptase domains of Ty1-copia group retroelements (Hirochika et al., 1992, Mol. Gen. Genet., 233, 209–216). Tos17 has a length of 4.3 kb and has two identical LTRs (long terminal repeats) of 138 bp and a PBS (primer binding site) which is complementary to the 3' end of the initiator methionine tRNA (Hirochika et al., 1996, supra). Transcription of Tos17 is strongly activated by tissue culture, and the copy number of Tos17 increases with time in culture. Its initial copy number in Nipponbare (a Japonica variety), which is used as a genome research model, is two. In plants regenerated from tissue culture, its copy number is increased to 5 to 30 (Hirochika et al., 1996, supra). Unlike class I transposons found in yeast and Drosophila, Tos17 undergoes random transposition in a chromosome and induces mutation in a stable manner. Therefore, Tos17 provides a useful tool in reverse genetics for analyzing the function of a gene in rice (Hirochika, 1997, Plant Mol. Biol. 35, 231–240; K. Shimamoto Ed., 1999, Molecular Biology of Rice, Springer-Verlag, 43–58).

DISCLOSURE OF THE INVENTION

Therefore, an object of the present invention is to reveal a gene encoding a protein capable of determining sensitivity to a salt stress and/or osmotic stress; manipulate sensitivity to a plurality of environmental stresses including a salt stress and an osmotic stress; select plants having different sensitivities; and provide a gene useful for production of plants having enhanced tolerance to these environmental stresses.

The present inventors found mutants having a high level of sensitivity to a salt stress among a number of rice gene destruction strains which were produced using the property of rice retrotransposon Tos17 that it is activated by culture to undergo transposition. This mutant exhibits traits, such as growth inhibition and morphological abnormality of an organ, under salt stress. The relationship between trait change and salt stress has been rigorously studied. As a result, it was found that trait change is attributed to mutation(s) of a gene capable of determining sensitivity to salt stress, and the present invention was completed.

The present invention relates to a polynucleotide, encoding a plant gene capable of controlling salt stress tolerance, wherein the polynucleotide includes a polynucleotide which has a nucleotide sequence encoding an amino acid sequence from methionine at position 1 to asparagine at position 243 of SEQ ID NO: 2 in the sequence listing, or which has a nucleotide sequence encoding the amino acid sequence having one or several amino acid deletions, substitutions and/or additions and is capable of controlling salt stress tolerance.

In one embodiment of this invention, the plant gene is further capable of controlling osmotic stress tolerance.

In one embodiment of this invention, the polynucleotide is derived from rice.

The present invention also relates to a polynucleotide, encoding a plant gene capable of controlling salt stress tolerance, wherein the polynucleotide includes a polynucleotide having a nucleotide sequence from A at position 233 to C at position 961 in SEQ ID NO: 1 in the sequence listing, or a nucleotide sequence hybridizable to the nucleotide sequence under stringent conditions.

In one embodiment of this invention, the plant gene is further capable of controlling osmotic stress tolerance.

In one embodiment of this invention, the polynucleotide is derived from rice.

BRIEF DESCRIPTION OF THE DRAWINGS

FIG. 3 shows a cDNA sequence (SEQ ID NO: 1) of a rice gene determining salt stress sensitivity.

FIG. 4 shows a putative amino acid sequence (SEQ ID NO: 2) of a protein encoded by a rice gene determining salt stress sensitivity.

BEST MODE FOR CARRYING OUT THE INVENTION

Figure 1:
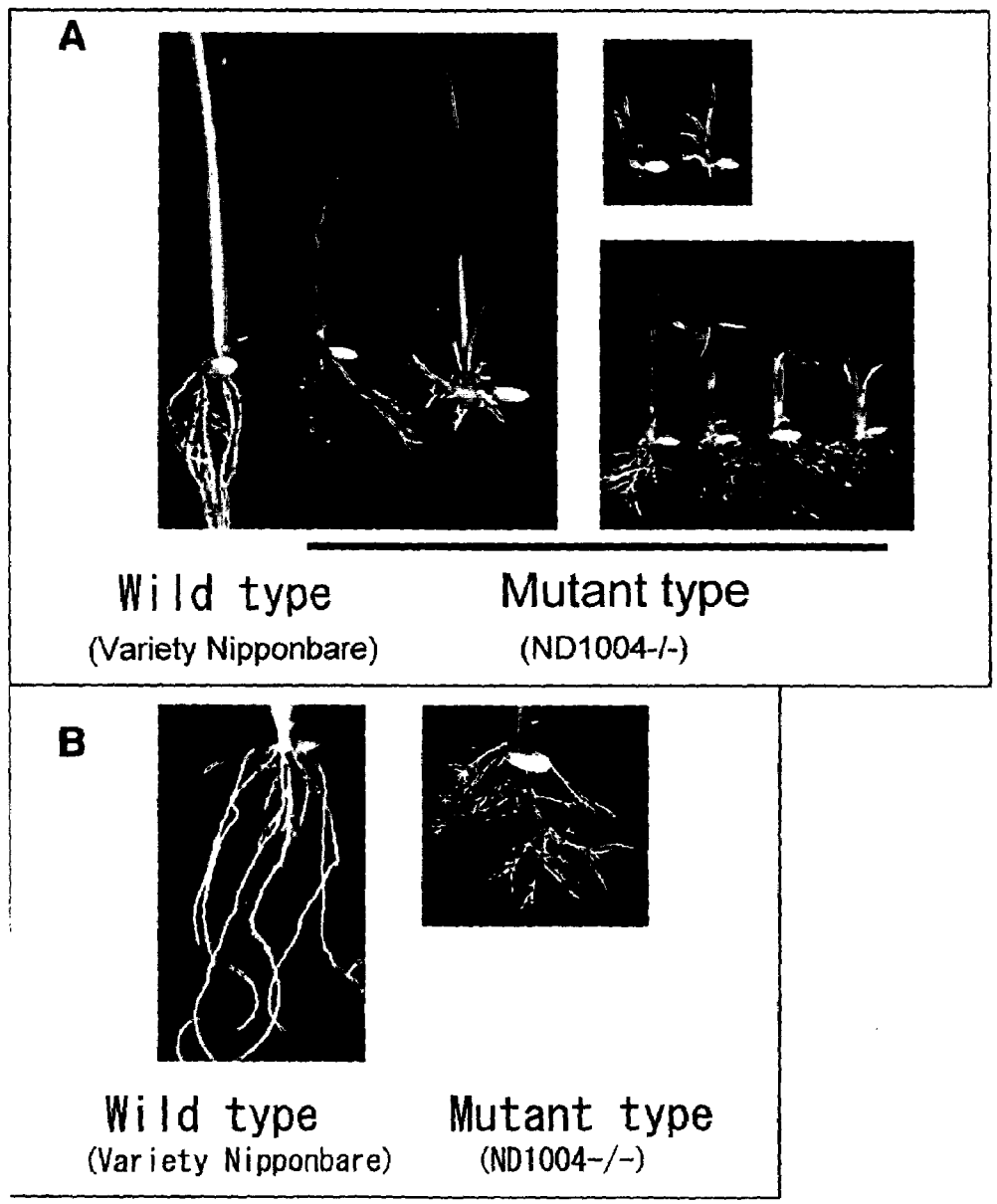
FIG. 1 shows photographs (A) indicating the morphology of shoots and roots of mutants highly sensitive to salt stress obtained from a redifferentiated Nipponbare strain and wild type seedlings as controls, and photographs (B) indicating the morphology of roots.

The present invention provides a novel plant gene which was isolated by using Tos17 and whose function was revealed.

The term "gene" as used herein refers to a structural unit carrying hereditary information and an element defining a trait. A gene may be defined as a hereditary functional unit specified by the base sequence of a certain region in polymer DNA or RNA. Therefore, a gene may be understood as a DNA or RNA which will be eventually translated into a protein, or a polynucleotide.

"Stress" as used herein refers to a factor which externally causes a change in the growth of plants. "Environmental stress" refers to a stress provided by a change in an external environment, including salts, high osmotic pressure, drying, high temperature, low temperature, intense light, air pollution, and the like.

According to the present invention, a polynucleotide encoding a plant gene controlling salt stress tolerance is provided. The term "salt stress" as used herein means that salt concentration is increased in a cultivation medium (e.g., soil, media which permit cultivation of plants (solid or liquid), etc.) to the extent that the growth of plants is adversely affected. Salts include any salt which leads to inhibition of water absorption in plants, including, for example, magnesium salts, chloride salts, aluminum salts, and the like. The term "salt stress tolerance" as used herein refers to tolerance to the above-described salt stresses. "Salt stress sensitivity" refers to sensitivity to the above-described salt stresses, for example, affected by an influence disadvantageous to growth. When a strain having "salt stress sensitivity" is grown in a cultivation medium (e.g., soil, media which permit cultivation of plants (solid or liquid), etc.) having an intermediate/low concentration (e.g., 50 to 300 mM, and preferably 100 to 150 mM) of salt, the strain may exhibit growth inhibition and morphological abnormality in plant organs and tissue. "Control salt stress tolerance" refers to suppressing or promoting expression of a gene involved in salt stress, or encoding a protein determining salt stress tolerance or controlling its operation.

The plant gene of the present invention may further control osmotic stress tolerance. "Osmotic stress" means that generation of osmotic pressure adversely affects the growth of plants. Osmotic pressure is involved in the growth of plant cells (water absorption) in which water is taken into the cell to increase the volume of the cell. In general, as osmotic pressure is increased, the water absorption power of plants is lowered. The term "osmotic stress tolerance" as used herein refers to tolerance to an osmotic stress. "Osmotic stress sensitivity" means a certain response to the above-described osmotic stress. When a strain having "osmotic stress sensitivity" is grown in a cultivation medium (e.g., soil, media which permit cultivation of plants (solid or liquid), etc.) and which causes high osmotic pressure (e.g., 50 to 600 mM, and preferably at least 150 mM in a mannitol equivalent), a plant body (particularly, roots) may exhibit significant growth inhibition. "Control osmotic stress tolerance" refers to suppressing or promoting expression of a gene involved in an osmotic stress, or encoding a protein determining osmotic stress tolerance or controlling its operation.

The polynucleotide of the present invention as mentioned above is a polynucleotide, including a polynucleotide having a nucleotide sequence encoding an amino acid sequence from methionine (Met) at position 1 to asparagine (Asn) at position 243 in SEQ ID NO: 2 in the sequence listing, or a nucleotide sequence encoding an amino acid sequence in which one or several amino acids are deleted from, substituted in, and/or added to the above amino acid sequence. In one embodiment, the polynucleotide of the present invention is a polynucleotide having a nucleotide sequence at position 233–961 of SEQ ID NO: 1 of the sequence listing. The polynucleotide of the present invention may further contain a nucleotide sequence (e.g., a non-translational region) out of (5' or 3' to) the above-described regions (the nucleotide sequence region encoding the amino acid sequence from methionine (Met) at position 1 to asparagine (Asn) at position 243 of SEQ ID NO: 2 or the nucleotide sequence region at position 233–961 of SEQ ID NO: 1). More preferably, the polynucleotide of the present invention consists of the full-length sequence at position 1–1154 of SEQ ID NO: 1. The polynucleotide of the present invention includes all degenerate isomers of SEQ ID NO: 1. The term "degenerate isomer" refers to DNA encoding the same polypeptide and having a degenerate codon(s). For example, for a DNA having the base sequence of SEQ ID NO: 1 in which a codon corresponding to a certain amino acid (e.g., Asn) thereof is AAC, a DNA in which the AAC is changed to the degenerate codon AAT is called a degenerate isomer.

The polynucleotide of the present invention has been obtained from a rice genomic DNA using Tos17 as a marker based on the finding of a mutant highly sensitive to a salt stress of a rice gene disruption strain produced using the property of rice retrotransposon Tos17 that it is activated by culture and undergoes transposition. Therefore, in one embodiment, the polynucleotide of the present invention is derived from rice.

Fragments and variants of the disclosed nucleotide sequences and proteins encoded thereby may be included in the present invention. The term "fragment" is intended to refer to a portion of a nucleotide sequence or a portion of an amino acid sequence, or a protein encoded thereby. A fragment of a nucleotide sequence can encode a protein fragment holding at least one functional biological activity of a native protein.

A variant of a protein encoded by the polynucleotide of the present invention is intended to refer to a protein modified from the native protein by at least one amino acid deletion (truncation) or addition at the N and/or C terminus of the protein; at least one amino acid deletion or addition at at least one site in the protein; or at least one amino acid substitution at at least one site in the protein. Such a variant may be generated by genetic polymorphism or artificial modification, for example.

The protein encoded by the polynucleotide of the present invention may be modified using various methods (including amino acid substitution, deletion, truncation, and insertion). These methods are generally known in the art. For example, a variant of the amino acid sequence of the protein encoded by the plant gene capable of controlling stress tolerance of the present invention may be prepared by mutagenesis. Methods for mutagenesis and modification of a nucleotide sequence are well known in the art, e.g., Kunkel (1985) Proc. Natl. Acad. Sci. USA 82:488–492; Kunkel et al. (1987) Methods in Enzymol. 154:367–382; U.S. Pat. No. 4,873,192; Walker and Gaastra ed. (1983) Techniques in Molecular Biology (MacMillian Publishing Company, New York) and their cited references. Guidance as to appropriate amino acid substitutions that do not affect biological activity of the protein of interest can be found in the model of Dayhoff et al. (1987) Atlas of Protein Sequence and Structure (Natl. Biomed. Res. Found. Washington, D.C.), which is herein incorporated by reference. Conservative substitution (e.g., one amino acid is substituted with another one having a similar property) may be preferable. Examples of such a substitution include a substitution between hydrophobic amino acids (Ala, Ile, Leu, Met, Phe, Pro, Trp, Tyr, and Val); a substitution between hydrophilic amino acids (Arg, Asp, Asn, Cys, Glu, Gln, Gly, His, Lys, Ser, and Thr); a substitution between amino acids having an aliphatic side chain (Gly, Ala, Val, Leu, Ile, and Pro); a substitution between amino acids having a side chain containing a hydroxyl group (Ser, Thr, and Tyr); a substitution between amino acids having a side chain containing a sulfur atom (Cys and Met); a substitution between amino acids having a side chain containing carboxylic acid and amide (Asp, Asn, Glu, and Gln); a substitution between amino acids having a side chain containing a base (Arg, Lys, and His); and a substitution between amino acids having a aromatic side chain (His, Phe, Tyr, and Trp).

Therefore, "one or several deletions, substitutions and/or additions" refers to as many amino acid substitution(s), deletion(s) and/or addition(s) as those caused by genetic polymorphism or artificial modification (including the above-described well-known methods). "One or several deletions, substitutions and/or additions" are any number of amino acids may be deleted from, added to, and/or substituted in the amino acid sequence of the protein as long as a protein having such modifications still has the function of the protein encoded by the polynucleotide of the present invention. It will be clearly understood by those skilled in the art that the influence of modifications, such as amino acid substitutions, deletions and/or additions, on activity may be dependent on the positions, extent, types, or the like of amino acids to be modified. Regarding the polynucleotide of the present invention, a number of amino acids may be deleted, substituted and/or added in the full-length amino acid sequence to satisfy the amino acid sequence identity defined below, as long as the function of the protein encoded by the polynucleotide of the present invention can be expressed, for example.

The polynucleotide encoding the plant gene capable of controlling salt stress tolerance of the present invention includes a polynucleotide having a nucleotide sequence encoding an amino acid sequence having at least 60%, preferably at least 65%, more preferably at least 70%, more preferably at least 75%, even more preferably at least 80%, still more preferably at least 90%, still even more preferably at least 95%, and most preferably at least 99% sequence identity to the amino acid sequence from Met at position 1 to Asn at position 243 in SEQ ID NO: 2 of the sequence listing as long as it can similarly salt stress tolerance.

The polynucleotide encoding the plant gene capable of controlling salt stress tolerance of the present invention includes a polynucleotide having a nucleotide sequence having at least 70%, preferably at least 75%, more preferably at least 80%, even more preferably at least 85%, still more preferably at least 90%, still even more preferably at least 95%, and most preferably at least 99% sequence identity to the nucleotide sequence encoding the amino acid sequence from Met at position 1 to Asn at position 243 in SEQ ID NO: 2 of the sequence listing (preferably, a nucleotide sequence from A at position 233 to C at position 961 in SEQ ID NO: 1) as long as it can similarly control salt stress tolerance.

As used herein, a "reference sequence" refers to a defined sequence used as a basis for a sequence comparison. A reference sequence may be a subset or the whole of the specified sequence; for example, a segment of a full-length cDNA or gene sequence or a complete DNA or gene sequence.

As used herein, a "comparison window"s includes reference to a contiguous and specified segment of a polynucleotide sequence, wherein the polynucleotide sequence in the comparison window may contain additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those skilled in the art understand that to avoid a high similarity to a reference sequence due to inclusion of gaps in the polynucleotide sequence, typically a gap penalty is introduced and is subtracted from the number of matches.

Methods of alignment of sequences for comparison are well-known in the art. Global optimal alignment of a reference sequence (the sequence of the present invention) and a subject sequence is preferably determined by homology analysis using BLAST (Altshul et al., 1997, Nucleic Acids Res., 25, 3389–3402). In a sequence alignment, the reference and subject sequences are both DNA sequences. An RNA sequence can be compared by converting U's to T's. The result of the global sequence alignment is in percent identity. The sequence alignment may be conducted using default parameters in the program.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted with other amino acid residues with similar chemical properties (e.g. charge or hydrophobicity) and therefore do not change the functional properties of the molecule. Where sequences differ in conservative substitutions, the percent sequence identity maybe adjusted upwards to correct for the conservative nature of the substitution. Sequences which differ by such conservative substitutions are said to have "sequence similarity" or "similarity". Means for making this adjustment are well-known to those skilled in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated with, e.g., the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may contain additions or deletions (i. e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. Those skilled in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes means sequence identity of normally at least 60%, more preferably at least 70%, 80%, 90%, and most preferably at least 95%.

The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Optionally, optimal alignment is conducted using the homology alignment algorithm of Needleman et al., J. Mol. Biol. 48: 443 (1970). A peptide is substantially identical to a second peptide, for example, where the two peptides differ only by a conservative substitution. Peptides which are "substantially similar" share sequences as noted above except that residue positions which are not identical may differ by conservative amino acid changes.

Fragments of the plant gene nucleotide sequence of the present invention capable of controlling salt stress tolerance, which encode a biologically active portion of a protein capable of controlling salt stress tolerance, encode at least 15, 25, 30, 50, 100, 125, 150, 175, 200, or 225 contiguous amino acids, or the overall amino acids present in the full-length protein of the present invention (e.g., 243 amino acids of SEQ ID NO: 2). In general, a fragment of the plant gene nucleotide sequence capable of controlling salt stress tolerance, which is used as a hybridization probe for a PCR primer, may not encode a biologically active portion of a protein capable of controlling salt stress tolerance in plants.

Polynucleotides encoding a plant gene capable of controlling salt stress tolerance derived from plants other than rice maybe included in the scope of the present invention. Such a polynucleotide may be isolated by, for example, conducting PCR using a primer designed based on the full-length or a portion of a disclosed nucleotide sequence and the genomic DNA of a selected plant as a template, followed by screening genomic DNA or cDNA libraries of the same plant using an obtained amplified DNA fragment as a probe. In this manner, methods such as PCR, hybridization, and the like can be used to identify such sequences based on their sequence identity to the sequence set forth herein. Sequences isolated based on their sequence identity to the sequences set forth herein or to fragments thereof are encompassed by the present invention.

In a hybridization technique, all or part of a known nucleotide sequence is used as a probe which selectively hybridizes an other corresponding nucleotide sequence present in a group of cloned genomic DNA fragments or cDNA fragments derived from a selected organism (i.e., genomic libraries or cDNA libraries). The hybridization probe may be genomic DNA fragments, cDNA fragments, RNA fragments, or other oligonucleotides, and may be labeled with a detectable group. (e.g., $^{32}P$) or any other detectable marker. Therefore, probes for hybridization can be made by labeling synthetic oligonucleotides based on the nucleotide sequence of the plant gene capable of controlling salt stress tolerance in plants of the present invention. Methods for preparation of probes for hybridization and construction of cDNA libraries and genomic libraries are generally known in the art and are disclosed in Sambrook et al. (1989) Molecular Cloning: A Laboratory Manual (2nd ed., Cold Spring Harbor Laboratory Press, Plainview, N.Y., which is herein incorporated by reference).

For example, all or a part of a nucleotide sequence encoding the plant gene capable of controlling salt stress tolerance disclosed herein can be used as a probe hybridizable to the corresponding plant gene sequence capable of controlling salt stress tolerance and the messenger RNA thereof. To achieve specific hybridization under various conditions, such a probe is unique to the plant gene sequence capable of controlling salt stress tolerance, and includes sequence having preferably at least about 10 nucleotides in length, and most preferably at least about 20 nucleotides in length. Such a probe can be used in PCR to amplify the plant gene sequence capable of controlling salt stress tolerance derived from a selected organism. Methods for PCR amplification are well known in the art (PCR Technology: Principles and Applications for DNA Amplification, H A Erlich ed., Freeman Press, New York, N.Y. (1992); PCR Protocols: A Guide to Methods and Applications, Innis, Gelfland, Snisky, and White ed., Academic Press, San Diego, Calif. (1990); Mattila et al. (1991) Nucleic Acids Res. 19: 4967; Eckert, K. A. and Kunkel, T. A. (1991) PCR Methods and Applications 1: 17; PCR, McPherson, Quirkes, and Taylor, IRL Press, Oxford, these are herein incorporated by reference). This technique can be used as a diagnostic assay to isolate additional encoding sequences from a desired organism or to determine the presence of an encoding sequence in an organism. The hybridization technique includes hybridization screening of plated DNA libraries (either plaques or colonys; e.g., Sambrook et al. (1989) Molecular Cloning: A Laboratory Manual (2nd ed., Cold Spring Harbor Laboratory Press, Plainview, N.Y.)).

The hybridization of the sequences may be conducted under stringent conditions. The terms "stringent conditions" or "stringent hybridization conditions" includes reference to conditions under which a probe will hybridize to its target sequence, to a detectably greater degree than other sequences (e. g., at least 2-fold over background). Stringent conditions are sequence-dependent and will be different in different circumstances. By controlling the stringency of the hybridization and/or washing conditions, target sequences can be identified which are 100% complementary to the probe. Alternatively, stringency conditions can be adjusted to allow some mismatching in sequences so that lower degrees of similarity are detected. Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) (pH 7.0 to 8.3) and the temperature is at least about 30° C. for short probes (e. g., 10 to 50 nucleotides) and at least about 60° C. for long probes (e. g., greater than 50 nucleotides). Stringent conditions may also be achieved with the addition of destabilizing agents (e.g., formamide). Exemplary stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary more stringent conditions include hybridization in 40 to 45% formamide, 1.0 M NaCl, 1% SDS at 37° C., and a wash in 0.5× to 1× SSC at 55 to 60° C. Exemplary even more stringent conditions include hybridization in 50% formamide, 1 M NaCl, 1% SDS at 37° C., and a wash in 0.1× SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984), Anal. Biochem., 138: 267–284: $T_m=81.5°$ C.+16.6(log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with at least 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those skilled in the art will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen (1993), Laboratory Techniques in Biochemistry and Molecular Biology Hybridization with Nucleic Acid Probes, Part I, Chapter 2 (Elsevier, N.Y.); and Ausubel, et al., Eds. (1995), Current Protocols in Molecular Biology, Chapter 2 (Greene Publishing and Wiley-Interscience, New York). Also See, Sambrook et al. (1989) Molecular Cloning: A Laboratory Manual (2nd ed., Cold Spring Harbor Laboratory Press, Plainview, N.Y., which is herein incorporated by reference).

The base sequence of the obtained gene can be determined by a nucleotide sequence analysis method known in the art or a commercially available automated sequencer.

The polynucleotide of the present invention is typically obtained in accordance with a method set forth herein, or may be obtained by chemical synthesis based on the sequences described in the present invention. For example, the polynucleotide of the present invention may be synthesized using a polynucleotide synthesizer commercially available from Applied BioSystems, Inc. (the present Perkin Elmer) in accordance with the instructions provided by the manufacturer.

As demonstrated in examples below, it is clear that a polynucleotide encoding the plant gene of the present invention determines sensitivity to a salt stress and an osmotic stress. It is known that responses of plants to a salt stress overlap responses to environmental stresses, such as drying, high osmotic pressure, low temperature, and the like (Tanpakushitsu Kakusan Koso [Protein/Nucleic acid/Enzyme] (1999) Vol. 44, 2147–2148/2188–2198; Curr. Opinion. Plant. Biol. (2001) vol. 4 241–246; Curr. Opinion. Plant. Biol. (2000) vol. 3 217–223; TRENDS in Plant Science (2001) Vol.6 66–71). It is highly probable that the polynucleotide of the present invention relates to a stress due to drying or low temperature. When the polynucleotide of the present invention exhibits its function, plants normally grow under stress conditions or the growth of plants is not adversely affected. However, when the polynucleotide of the present invention does not function for any reason, the growth of plants under stress conditions may be inhibited.

A desired property of the polynucleotide produced by the above-described genetic engineering method or chemical synthesis method, i.e., capability of controlling salt stress tolerance, can be confirmed as follows. Specifically, the obtained polynucleotide is introduced into salt stress sensitive plants (e.g., a strain ND1004(-/-) obtained in Example 1 below) with techniques well known in the art. If salt stress tolerance is restored, the presence of the desired activity, i.e., an action of controlling salt stress tolerance, can be confirmed. The presence of an action of controlling salt stress tolerance may be confirmed by substantially the same procedure as described in Example 5. For example, it is assumed that the polynucleotide is introduced into the strain ND1004(-/-). If the strain ND1004(-/-) exhibits substantially the same salt stress tolerance as that of a wild type plant as described in Example 5, the presence of salt stress tolerance is confirmed. "Exhibit substantially equivalent salt stress tolerance as that of a wild type plant" may mean that no significant difference is observed in the growth of plants, to which the polynucleotide of the present invention is introduced, under salt stress conditions and no-salt stress conditions as shown in Example 5. Note that "salt stress conditions" as used herein means that plants can be grown in the cultivation medium (e.g., soil, media which permit cultivation of plants (solid or liquid), etc.) having an intermediate/low concentration (e.g., 50 to 300 mM, and preferably 100 to 150 mM) of salt as mentioned above.

Therefore, the polynucleotide of the present invention may be used to manipulate the sensitivity of plants to the above-described stresses including salt stress and osmotic stress or to select plants having different sensitivities to the stress (e.g., by screening various plant strains using a probe or a primer based on the whole or a part of the polynucleotide having the sequence of the present invention).

The polynucleotide of the present invention can be used to produce plants having enhanced tolerance to the above-described stresses. These plants are preferable if they are useful for agriculture. Development of such stress tolerant plants is expected to provide a reduction in agricultural damage due to environmental stresses and beneficial effects, such as an increase in crop yield due to extension of cultivation area and preservation of the environment.

The polynucleotide of the present invention may be ligated in a native or modified form with an appropriate plant expression vector using a method well known to those skilled in the art, and the vector may be introduced into a plant cell using a known gene recombination technique. The gene is incorporated in the DNA of a plant cell. The DNA of a plant cell includes DNA contained in various organelles (e.g., mitochondria and chloroplasts) as well as chromosomes.

As used herein, a "plant expression vector" refers to a nucleic acid sequence to which various regulatory elements, such as a promoter which regulates expression of the gene of the present invention, are operatively linked in a host plant cell. The term "control sequence" as used herein refers to a DNA sequence having a functional promoter and any related transcription element (e.g., an enhancer, a CCAAT box, a TATA box, and a SPI site). The term "operably linked" as used herein indicates that a polynucleotide is linked to a regulatory element which regulates expression of a gene, such as a promoter or an enhancer, so that the gene can be expressed. The plant expression vector may preferably include plant gene promoters, terminators, drug-resistance genes, and enhancers. It is well known to those skilled in the art that the type of an expression vector and the type of a regulatory element used may be changed depending on the host cell. A plant expression vector used in the present invention may have a T-DNA region. The T-DNA region can enhance the efficiency of gene introduction, particularly when Agrobacterium is used to transform a plant.

The term "plant gene promoter" as used herein refers to a promoter which is expressed in plants. A plant promoter fragment can be employed which will direct expression of a polynucleotide of the present invention in all tissues of a regenerated plant. Examples of a promoter for structural expression include a promoter for nopaline synthase gene (Langridge, 1985, Plant Cell Rep. 4, 355), a promoter for producing cauliflower mosaic virus 19S-RNA (Guilley, 1982, Cell 30, 763), a promoter for producing cauliflower mosaic virus 35S-RNA (Odell, 1985, Nature 313, 810), rice actin promoter (Zhang, 1991, Plant Cell 3, 1155), a maize ubiquitin promoter (Cornejo 1993, Plant Mol. Biol. 23, 567), and a REXφ promoter (Mitsuhara, 1996, Plant Cell Physiol. 37, 49).

Alternatively, the plant promoter can direct expression of a polynucleotide of the present invention in a specific tissue or may be otherwise under more precise environmental or developmental control. Such promoters are herein referred to as "inducible" promoters. Examples of inducible promoters include promoters which are inducible by environmental conditions, such as light, low temperature, high temperature, dryness, ultraviolet irradiation, or spray of a specific compound. Examples of such promoters include a promoter for a gene encoding ribulose-1,5-diphosphate carboxylase small subunit which is induced by light irradiation (Fluhr, 1986, Proc. Natl. Acad. Sci. USA 83, 2358), a promoter for rice lip19 gene inducible by low temperature (Aguan, 1993, Mol. Gen. Genet. 240, 1), promoters for rice hsp72 and hsp80 genes inducible by high temperature (Van Breusegem, 1994, Planta 193, 57), a promoter for the rab16 gene of *Arabidopsis thaliana* inducible by dryness (Nundy, 1990, Proc. Natl. Acad. Sci. USA 87, 1406), and a promoter for maize alcohol dehydrogenase gene inducible by ultraviolet irradiation (Schulze-Lefert, 1989, EMBO J. 8, 651). A promoter for the rab16 gene is inducible by spraying abscisic acid which is a plant hormone.

A "terminator" is a sequence which is located downstream of a region encoding a protein of a gene and which is involved in the termination of transcription when DNA is transcribed into mRNA, and the addition of a polyA sequence. It is known that a terminator contributes to the stability of mRNA, and has an influence on the amount of gene expression. Examples of such a terminator include, but are not limited to, a CaMV35S terminator and a terminator for the nopaline synthetase gene (Tnos).

A "drug-resistant gene" is desirably one that facilitates the selection of transformed plants. The neomycin phosphotransferase II (NPTII) gene for conferring kanamycin resistance, the hygromycin phosphotransferase gene for conferring hygromycin resistance, and the like may be preferably used. The present invention is not so limited.

An "enhancer" may be used so as to enhance the expression efficiency of a gene of interest. As such an enhancer, an enhancer region containing an upstream sequence within the CaMV35S promoter is preferable. A plurality of enhancers may be used.

Plant expression vectors as described above may be prepared using a gene recombination technique well known to those skilled in the art. In addition to vectors used in the Examples below, in construction of a plant expression vector, pBI vectors or pUC vectors are preferably used. The present invention is not so limited.

A plant material for DNA introduction can be appropriately selected from leaves, stems, roots, tubers, protoplasts, calluses, pollen, embryos, shoot primordium, according to the introduction method or the like. A "plant cell" may be any plant cell. Examples of a "plant cell" include cells of tissues in plant organs, such as leaves and roots; callus; and suspension culture cells. The plant cell may be in any form of a culture cell, a culture tissue, a culture organ, or a plant. Preferably, the plant cell is a culture cell, a culture tissue, or a culture organ. More preferably, the plant cell is a culture cell.

A plant culture cell, to which DNA is introduced, is generally a protoplast. DNA is introduced to a plant culture cell by a physicochemical method, such as an electroporation method and a polyethylene glycol method. A plant tissue, to which DNA is introduced, is a leaf, a stem, a root, a tuber, a callus, pollen, an embryo, shoot primordium, preferably a leaf, a stem, and a callus. DNA is introduced into a plant tissue by a physico chemical method, such as a biological method using a virus or Agrobacterium, or a particle gun method. The method using Agrobacterium is disclosed, for example, in Nagel et al. (Microbiol. Lett., 67, 325 (1990)). In this method, a plant expression vector is first used to transform Agrobacterium (e.g., by electroporation), and then the transformed Agrobacterium is introduced into a plant tissue by a well-known method, such as a leaf disc method. These methods are well known in the art. A method suitable for a plant to be transformed can be appropriately selected.

A cell, into which a plant expression vector has been introduced, is selected for drug resistance, such as kanamycin resistance. The selected cell can be regenerated to a plant by a commonly used method.

A plant cell, into which a polynucleotide of the present invention has been introduced, can be regenerated to a plant by culturing the plant cell in redifferentiation medium, hormone-free MS medium, or the like. A young rooted plant can be grown to a plant by transferring it to soil, followed by cultivation. Redifferentiation methods vary depending on the type of a plant cell. Redifferentiation methods for various plants are described: rice (Fujimura, 1995, Plant Tissue Culture Lett. 2, 74); maize (Shillito, 1989, Bio/Technol. 7, 581; Gorden-Kamm, 1990, Plant Cell 2, 603); potato (Visser, 1989, Theor. Appl. Genet. 78, 594); and tobacco (Nagata, 1971, Planta 99, 12).

Expression of an introduced gene of the present invention in a regenerated plant can be confirmed by a method well known to those skilled in the art. This confirmation can be carried out using, for example, Northern blotting. Specifically, total RNA is extracted from a plant leaf, is subjected to electrophoresis on denaturing agarose, and is blotted to an appropriate membrane. This blot is subjected to hybridization with a labeled RNA probe complementary to a portion of the introduced gene, thereby detecting mRNA of a gene of the present invention.

Plants which can be transformed using a polynucleotide of the present invention include any plant to which a gene can be introduced. As used herein, the term "plant" includes reference to whole plants, plant organs (e.g., leaves, stems, roots, etc.), seeds, plant propagators (e.g., pollen), and plant cells, and progeny of same. Plant cells as used herein include, without limitation, seeds, suspension cultures, embryos, meristematic regions, callus tissue, leaves, roots, shoots, gametophytes, sporophytes, pollen, and microspores. The term "plant" includes monocotyledonous and dicotyledonous plants. Such plants include any useful plants, particularly crop plants, vegetable plants, and flowering plants of garden varieties. Preferable plants include, but are not limited to, rice, maize, sorghum, barley, wheat, rye, *Echinochloa crus-galli*, foxtail millet, asparagus, potato, Japanese white radish, soybean, pea, rapeseed, spinach, tomato, and petunia. The most preferable plant to which the present invention is applied is rice, particularly Japonica rice.

Examples of types of plants that can be used in the manufacturing method of the present invention include plants in the families of Solanaceae, Poaeae, Brassicaceae, Rosaceae, Leguminosae, Curcurbitaceae, Lamiaceae, Liliaceae, Chenopodiaceae and Umbelliferae.

Examples of plants in the Solanaceae family include plants in the *Nicotiana, Solanum, Datura, Lycopersicon* and *Petunia* genera. Specific examples include tobacco, eggplant, potato, tomato, chili pepper, and petunia.

Examples of plants in the Poaeae family include plants in the *Oryza, Hordenum, Secale, Saccharum, Echinochloa* and *Zea* genera. Specific examples include rice, barley, rye, *Echinochloa crus-galli*, sorghum, and maize.

Examples of plants in the Brassicaceae family include plants in the *Raphanus, Brassica, Arabidopsis, Wasabia*, and

*Capsella* genera. Specific examples include Japanese white radish, rapeseed, *Arabidopsis thaliana,* Japanese horseradish, and *Capsella bursa-pastoris.*

Examples of plants in the Rosaceae family include plants in the *Orunus, Malus, Pynus, Fragaria,* and *Rosa* genera. Specific examples include plum, peach, apple, pear, Dutch strawberry, and rose.

Examples of plants in the Leguminosae family include plants in the *Glycine, Vigna, Phaseolus, Pisum, Vicia, Arachis, Trifolium, Alfalfa,* and *Medicago* genera. Specific examples include soybean, adzuki bean, kidney bean, pea, fava bean, peanut, clover, and bur clover.

Examples of plants in the Curcurbitaceae family include plants in the *Luffa, Curcurbita,* and *Cucumis* genera. Specific examples include gourd, pumpkin, cucumber, and melon.

Examples of plants in the Lamiaceae family include plants in the *Lavandula, Mentha,* and *Perilla* genera. Specific examples include lavender, peppermint, and beefsteak plant.

Examples of plants in the Liliaceae family include plants in the *Allium, Lilium,* and *Tulipa* genera. Specific examples include onion, garlic, lily, and tulip.

Examples of plants in the Chenopodiaceae family include plants in the *Spinacia* genera. A specific example is spinach.

Examples of plants in the Umbelliferae family include plants in the *Angelica, Daucus, Cryptotaenia,* and *Apitum* genera. Specific examples include Japanese udo, carrot, honewort, and celery.

The nomenclature used hereafter and the laboratory procedures described hereafter often involve well known and commonly employed procedures in the art. Standard techniques are used for recombinant methods, polynucleotide synthesis, and cell culture. The techniques and procedures are generally performed according to conventional methods in the art and various general references (see, generally, Sambrook et al. Molecular Cloning: A Laboratory Manual, 2nd ed. (1989) Cold Spring Harbor Laboratory Press, Cold Spring Harbor, N.Y., which is incorporated herein by reference).

Hereinafter, the present invention will be described by way of examples. The present invention is not so limited. Materials, reagents, and the like used in the examples are available from commercial sources, unless otherwise mentioned.

EXAMPLES

Example 1

Activation of Tos17 by Culture and Characterization of Resultant Mutants

Mature seeds of "Nipponbare", "Hitomebore", or the like (varieties of species *Japonica*) were used as starting material to conduct callus initiation culture and cell suspension culture, as described in Hirochika et al., 1996, Proc. Natl. Acad. Sci. USA, 93, 7783–7788) (supra). Culture conditions for activating Tos17 used in gene disruption were determined in accordance with Otsuki's method (1990) (Rice protoplast culture, Agriculture, Forestry and Fisheries Technical Information Society).

Briefly, mature seeds of rice were cultured in MS medium containing 2,4-dichlorophenoxyacetic acid (2,4-D) (Otsuki (1990), supra) (25° C., 1 month) so as to induce calluses. The resultant calluses were cultured in N6 liquid medium containing 2,4-D (Otsuki (1990), supra) for 5 months, and were transferred to redifferentiation medium (Otsuki (1990), supra) to obtain redifferentiated rice (first generation (R1) plant).

About 20 R1 seeds were recovered from each plant. The seeds were sterilized with 1.0% sodium hypochlorite, followed by thoroughly washing. The seeds were immersed in water at 25° C. for 24 hours. Thereafter, the seeds were plated on MS solid medium (described in Murashige and Skoog, 1962, Physiol. Plant., 15, 473–497) containing 150 mM sodium chloride, which provided salt stress conditions. Second generation (R2) plants were obtained and were subjected to morphological analysis. The phenotype of each plant of the R2 group was carefully observed over 3 to 4 weeks after germination. As a result, among the R2 group of the strain ND1004 (variety: Nipponbare), a mutant was found, which had significant growth inhibition in its shoot and root (seedlings other than the left-most one in FIG. 1A), and significant branching of its root (a seedling to the right of FIG. 1B) under the salt stress conditions as compared to a wild type ND1004. On the other hand, the growth of the wild type ND1004 was not significantly inhibited under the salt stress conditions (the left-most seedling in FIG. 1A; and a seedling to the left of FIG. 1B).

Therefore, gene destruction due to transition of Tos17 was inferred to be responsible for such expression of the phenotype under the salt stress conditions.

Example 2

Isolation of Flanking Sequence to Tos17

In order to find a gene which controls the phenotype observed in Example 1, a flanking sequence to Tos17, which had been transferred into genomic DNA, was isolated.

DNA was prepared from the R2 rice (strain ND1004) obtained in Example 1 by a CTAB method (Murray and Thompson, 1980, Nucleic Acids Res. 8, 4321–4325). A Tos17 target site sequence was amplified by reverse PCR using total DNA as previously described (Hirochika et al., 1996, supra; and Sugimoto et al., 1994, Plant J., 5, 863–871).

Briefly, about 0.5. mu.g of total DNA from a mutant plant (strain ND1 004–/–), in which Tos17 was inserted into a target site by transposition, was initially digested with Xbal. The digested DNA was extracted with phenol/chloroform, followed by ethanol precipitation for purification. Thereafter, T4 DNA ligase was used to carry out ligation at 12. degree. C. overnight with a total volume of 300. mu.l. Ligated DNA was purified, one third of which was used as a template for PCR. An amplification reaction was carried out by PCR using the following primer: Tos17-3911F, GAGAGCATCATCGGTTACATCTTCTC (SEQ ID NO: 3) and Tos17-xbal-R, CATGAAATAGATCCATGTATATCT (SEQ ID NO: 4). A reverse PCR product was cloned in pCR2.1-TOPO vector (Invitrogen), followed by sequencing using a sequencer (ABI, model 310). Based on the resultant sequence, a primer OF, GCCATCACAAATCAGCAAGC (SEQ ID NO: 5), and a primer 3R, ATGGATTGAAGGC-CAAGCCAC (SEQ ID NO: 6), were designed. These primers were used to carry out reverse PCR using total DNA of a normal plant (without tissue culture) so that the target site of Tos17 insertion was amplified. The target site was sequenced as mentioned above.

Example 3

Structural Analysis of Causative Gene in Mutant

RNA was prepared from seedlings of wild type rice (Nipponbare) grown in soil for 11 days in the manner below. Initially, ISOGEN solution was used to extract total RNA from the seedlings. The total RNA was applied to an oligo(dt)cellulose column included in a mRNA purification kit (Stratagene) to obtain poly(A) mRNA. cDNA was synthesized from the resultant poly(A) mRNA by a commonly used method. A cDNA library was constructed in HybriZAP-2.1 vectors (Stratagene). The cDNA library had an infection ability of $5 \times 10^5$ plaques. In vivo cleavage of pBluescript plasmid including cDNA inserted fragments was conducted using *Escherichia coli* strain XL1-Blue MRF2.

The cDNA library was subjected to screening in accordance with a method described in Molecular Cloning, A Laboratory Manual (Sambrook et al., 1989), where the reverse PCR products of the flanking sequence to Tos17, which were obtained in Example 2, were used as probes.

From the cDNA library, nine cDNA clones exhibiting a strong hybridization signal were obtained.

The longest cDNA of the nine clones, having a size of about 1.2 kb, was sequenced using the sequencer 3100 (Applied Biosystems (ABI)) in both directions, followed by homology analysis using open reading frame (ORF) and BLAST (Altshul et al., 1997, Nucleic Acids Res., 25, 3389–3402) and analysis using Mac Vector 6.0 program (Teijin System Technology).

According to the sequencing analysis, the longest cDNA clone was 1154 bp in length (SEQ ID NO: 1). The mRNA analysis using the Mac Vector 6.0 package identified the longest open reading frame of 729 bp encoding a protein consisting of 243 amino acids (SEQ ID NO: 2). The cDNA sequence of 1154 bp indicated by SEQ ID NO: 1 is shown in FIG. 3. The open reading frame is located at position 233–961 of the cDNA sequence. A putative amino acid sequence (SEQ ID NO: 2) of a polypeptide encoded by the open reading frame is shown in FIG. 4.

Example 4

Search for Separate Mutant Strains

In Example 1, the mutant strain ND1004 was selected, which exhibited growth inhibition in its shoot and root under the salt stress conditions. In Example 3, the candidate gene which controls the phenotype was isolated. If the same phenotype is observed in other separate mutant strains having Tos17 insertion mutation in the same gene, it is concluded that the gene isolated in Example 3 is a gene controlling the phenotype. In order to confirm this, separate mutant strains were screened in the following manner.

DNA was prepared from a redifferentiated rice group as in Example 2. The base sequence of cDNA obtained in Example 3 was used to design the following four primers, and PCR was carried out using the above-described DNA as a template: GTCTGGCCAGTCGTGCAATG (SEQ ID NO: 7); CTGCTGGCAAGAGGGCTGAT (SEQ ID NO: 8); TGGGTTCTTGGTGGCCTCAT (SEQ ID NO: 9); and GCCAAGCCACTGAAGCCATI (SEQ ID NO: 10). PCR screening for mutants was carried out in accordance with a method described in Akio Miyao and Hirohiko Hirochika (2001), lne-no-Tos17-niyoru-Idenshihakaiho [Gene Destruction Method Using rice Tos17], Saibo-Kogaku-Bessatsu [Special Issue of Cellular Engineering] "Shokubutsu-no-Genomu-saiensu-pur-otokoru [Protocol for Plant Genome Science", Shujyunsha, 73–81. As a result, a mutant strain NC8328 (derived from the variety Nipponbare) was obtained.

A Tos17 flanking sequence database (http://pc7080.abr.affrc.go.jp/~miyao/pub/Tos17/) was searched using the cDNA sequence described in FIG. 3 as a query. As a result, another mutant strain H0851 (derived from the variety Hitomebore) was identified.

Figure 2:
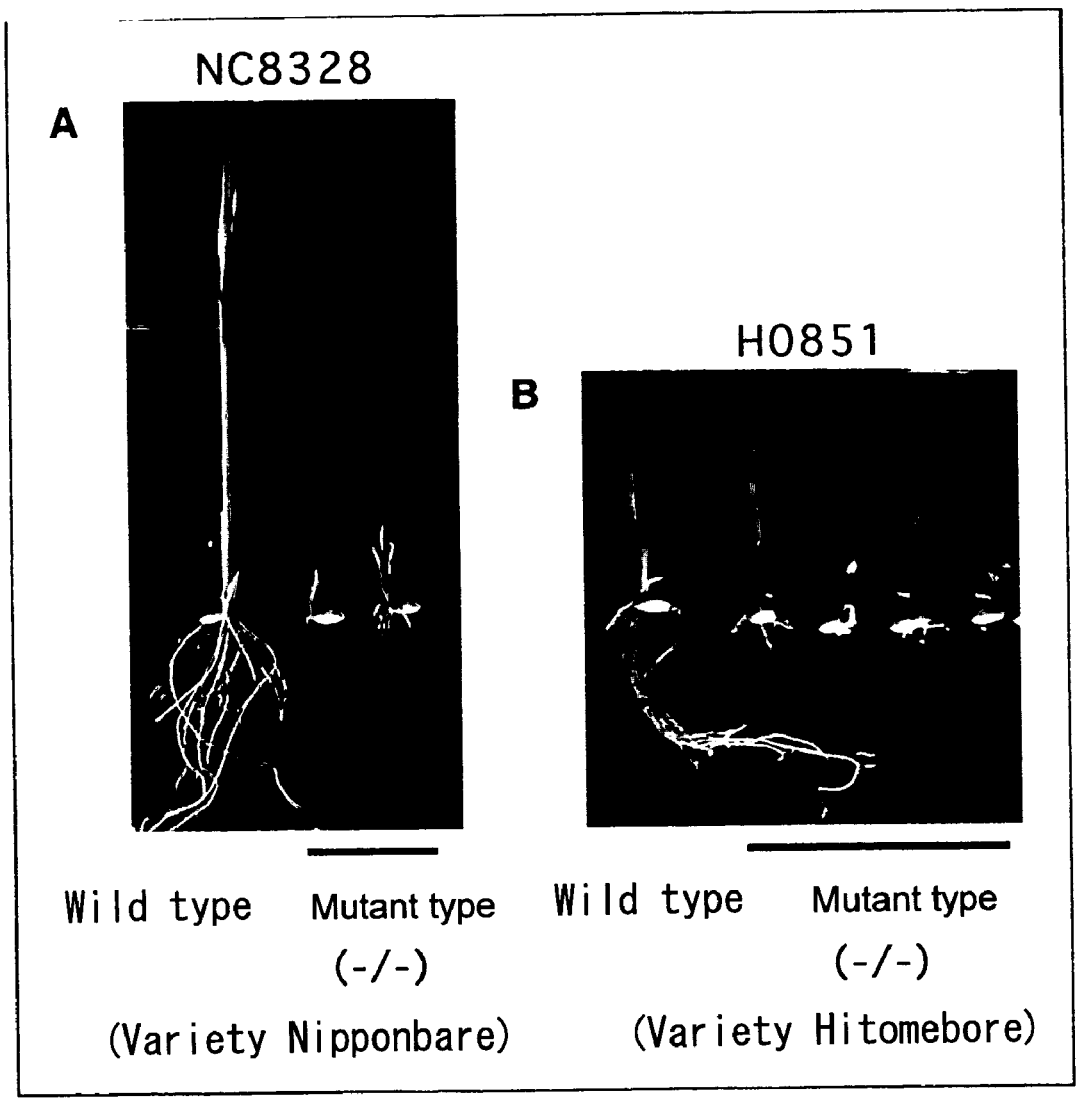
FIG. 2 shows photographs indicating the morphology of shoots and roots of mutants highly sensitive to salt stress separately obtained from a redifferentiated Nipponbare strain (A) and a redifferentiated Hitomebore strain and wild type seedlings as controls (B).

When these strains were grown under the salt stress conditions as described in Example 1, growth inhibition and morphological abnormality were observed in their shoots and roots (FIG. 2A (NC8328; the left-most plant indicates a wild type, and the middle and right plants indicate mutant types) and FIG. 2B (H0851; the left-most plant indicates a wild type, and four other seedlings were of a mutant type)).

Example 5

Evaluation of Salt Stress Sensitivity

In this example, a relationship between the gene obtained in Examples 2 to 4 and salt stress sensitivity was studied. The Nipponbare strain ND1004 was selected as a strain having this gene while the strain ND1004−/− was used as a mutant in which the gene was destroyed.

Individuals having the normal gene and mutants having the destroyed gene were separated in the R2 generation of the strain ND1004. The former was called strain ND1004+/+ while the latter was called strain ND1004−/− in experiments below. Southern analysis was carried out to determine whether the plant was a mutant. Specifically, DNA was extracted from the R2 generation strain ND1004 plant. The DNA was cleaved with the restriction enzyme XbaI, followed by agarose electrophoresis. The DNA was transcribed to a nylon membrane. Thereafter, hybridization was carried out using the gene labeled with $^{32}P$ as a probe so as to confirm the mutation of the gene. An individual exhibiting a mutant type band pattern is called strain ND1004−/−. The above-described analysis was carried out under conditions described in Molecular Cloning, A Laboratory Manual (Sambrook et al., 1989).

Figure 5:
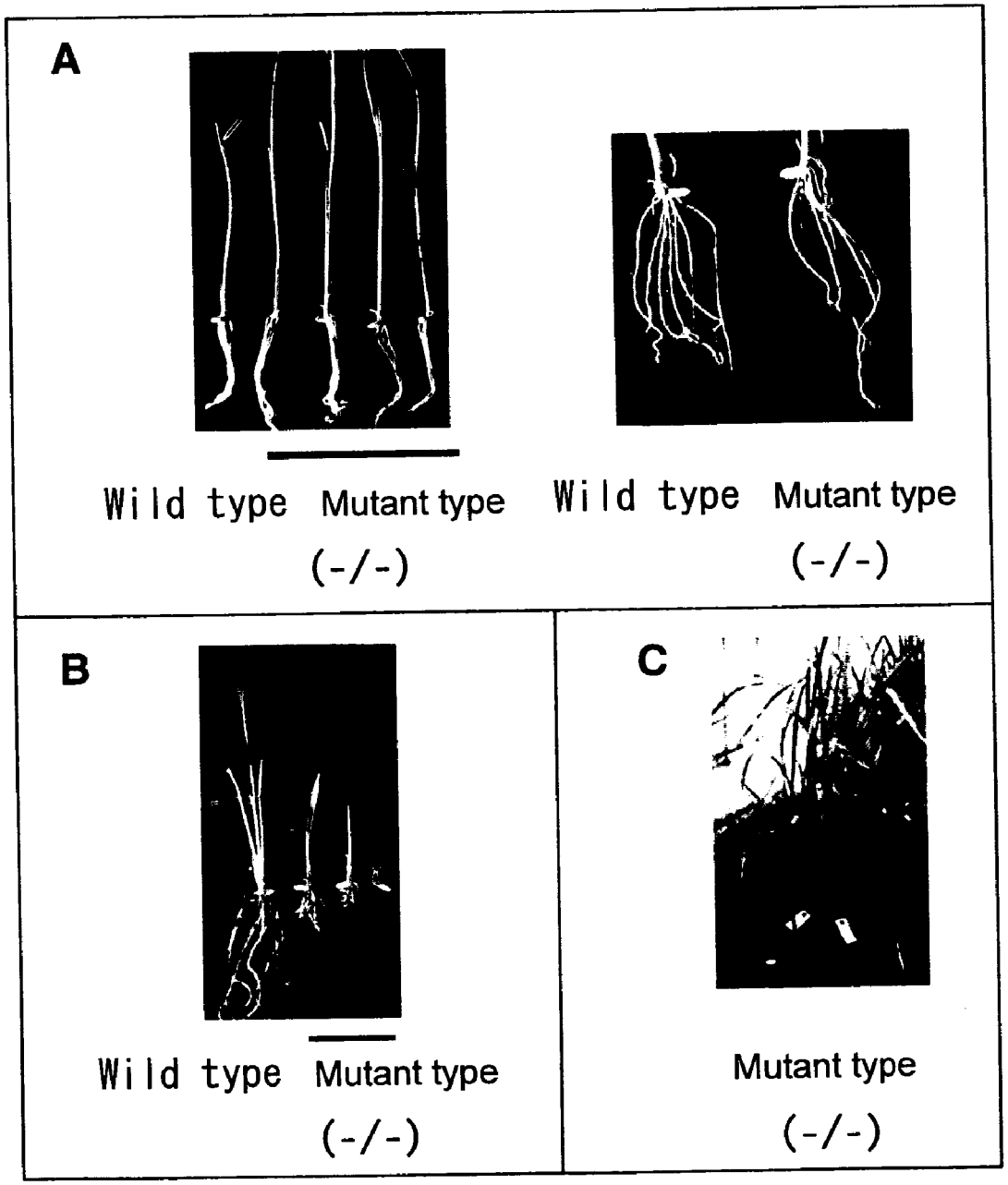
FIG. 5 shows photographs indicating the morphology of shoots and roots of wild types and mutant types germinated and grown in medium without sodium chloride (A) and medium with sodium chloride (B), and the morphology of growth of a mutant type grown in normal soil.

Seeds of the wild type ND1004 and the mutant type ND1004−/− (about 30 seeds for each plant) were sterilized with 1.0% sodium hypochlorite, followed by thoroughly washing. The seeds were immersed in water at 25° C. for 24 hours. Thereafter, the seeds were plated on MS solid medium (described in Murashige and Skoog, supra) containing 0 mM and 150 mM sodium chloride. The seeds were aseptically germinated and grown at 25° C. for 18 days in the light for 14 hours and in the dark for 10 hours. The growth of these plants is shown in FIGS. 5A and B. FIG. 5A shows the shoots and roots (left) and roots (right) of the wild type and the mutant type in media without sodium chloride (in the left photograph, the left-most plant is of the wild type, and the others are of the mutant type; and in the right photograph, the left plant is of the wild type and the right plant is of the mutant type). B shows the shoots and roots of a wild type (left most) and mutant types (three other individuals) grown in media containing sodium chloride. There was no significant difference observed in the morphology of shoots and roots of the wild type strain ND1004 between the salt stress conditions and the non-salt stress conditions, though the growth of the wild type strain ND1004 was slightly retarded (FIGS. 5A and 5B). In the mutant type ND1004−/− under the salt stress conditions, significant growth inhibition was observed in the shoot and the root, and morphological abnormality was observed in the root (FIG. 5B). Such growth inhibition and morphological abnormality were not observed under no-stress conditions (FIG. 5A).

Further, when this mutant type was germinated and grown in soil without salt stress (in a greenhouse for 3 months), it grew normally (FIG. 5C).

Therefore, sensitivity to salt stress was expressed by destruction of the gene. This indicates that the gene determines the sensitivity to salt stress.

Example 6

Evaluation of Sensitivity to Osmotic Stress

In this example, the relationship between the gene obtained in Examples 2 to 4 and osmotic stress sensitivity was studied. The Nipponbare strain ND1004 was selected as a strain having this gene while the strain ND1004−/− was used as a mutant in which the gene was destroyed.

Figure 6:
FIG. 6 shows a photograph indicating the morphology of growth of shoots and roots of wild types and a mutant type grown in mannitol-containing medium.

Seeds of the wild type ND1004 and the mutant type ND1004−/− (about 30 seeds for each plant) were sterilized with 1.0% sodium hypochlorite, followed by thoroughly washing. The seeds were immersed in water at 25° C. for 24 hours. Thereafter, the seeds were aseptically germinated and grown in MS solid medium (described in Murashige and Skoog, supra) without mannitol for 11 days under the same conditions as described in Example 5. An upper portion of the shoot and the root of a seedling grown for 11 days were cut and removed (a cut portion is indicated by arrows in FIG. 6). The remaining tissue section was transferred to MS solid medium containing 150 mM mannitol, and was grown for further 7 days under the same conditions as above. Whereas roots were newly generated and normally grown in the wild type, significant growth inhibition was observed in newly generated roots of the mutant type (the right plant indicates the mutant type, and the remaining two plants indicate the wild types).

Therefore, sensitivity to osmotic stress was also expressed by destruction of the gene. This indicates that the gene determines the sensitivity to osmotic stress.

The above-described examples illustrate various aspects of the present invention, and how a specific oligonucleotide of the present invention is produced and used. The present invention is not so limited.

INDUSTRIAL APPLICABILITY

A novel polynucleotide capable of controlling environmental stress tolerance, which is applicable to breeding of plants, is provided. Further, a polynucleotide useful for manipulation of sensitivity to environmental stress, selection of plants having different sensitivities, and enhancement of tolerance to environmental stress, is provided.

The invention claimed is:

1. An isolated polynucleotide, encoding a plant gene capable of promoting salt stress tolerance, wherein the isolated polynucleotide includes a polynucleotide which has a nucleotide sequence encoding an amino acid sequence from methionine at position 1 to asparagine at position 243 of SEQ ID NO: 2, or a polynucleotide capable of hybridizing to the isolated polynucleotide under stringent conditions comprising 50% formamide, 1 M NaCl, 1% SDS at 31° C., and a wash in 0.1×SSC at 60 to 65° C., and is capable of promoting salt stress tolerance.

2. An isolated polynucleotide according to claim 1, wherein the plant gene is further capable of promoting osmotic stress tolerance.

3. An isolated polynucleotide according to claim 1, wherein the isolated polynucleotide is derived from rice.

4. An isolated polynucleotide, encoding a plant gene capable of promoting salt stress tolerance, wherein the isolated polynucleotide includes a polynucleotide having a nucleotide sequence from A at position 233 to C at position 961 in SEQ ID NO: 1, or a nucleotide sequence hybridizable to the nucleotide sequence under stringent conditions comprising 50% formamide, 1 M NaCl, 1% SDS at 31° C., and a wash in 0.1×SSC at 60 to 65° C.

5. An isolated polynucleotide according to claim 4, wherein the plant gene is further capable of promoting osmotic stress tolerance.

6. An isolated polynucleotide according to claim 4, wherein the isolated polynucleotide is derived from rice.

* * * * *

UNITED STATES PATENT AND TRADEMARK OFFICE
CERTIFICATE OF CORRECTION

PATENT NO. : 7,034,139 B2 Page 1 of 1
APPLICATION NO. : 10/344980
DATED : April 25, 2006
INVENTOR(S) : Hirochika et al.

It is certified that error appears in the above-identified patent and that said Letters Patent is hereby corrected as shown below:

On Title Page, Item (54) Col. 1 should read,

NOVEL RICE GENE FOR CONTROLLING TOLERANCE TO SALT STRESS

Signed and Sealed this

Twenty-fifth Day of July, 2006

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 1154
<212> TYPE: DNA
<213> ORGANISM: Oryza sativa
<220> FEATURE:
<221> NAME/KEY: CDS
<222> LOCATION: (233)..(964)

<400> SEQUENCE: 1
aaaatttccc ctttcctctc cacgccaaga aacgcaaaac ccccacgccg accaaggcga      60
gaagcgccgc cgccgaatcg aaccgcgatc gcgcccttct cccgccgccc ccgcgcgctc     120
ttctcctcct cgtcctcgac gccgctgtgc cggagtttag gcggagatcg atccggagcg     180
gggtttctct tctacctggc aaggttgagg aagaaaagct tgctgatttg tg atg gct     238
                                                          Met Ala
                                                          1 gcc cca act gca aca gct gtt ttt ctt gat gag aac ctg cat atc cat       286
Ala Pro Thr Ala Thr Ala Val Phe Leu Asp Glu Asn Leu His Ile His
        5                  10                  15 agg ggg cct gct ggc aag agg gct gat gga ttg aag gcc aag cca ctg       334
Arg Gly Pro Ala Gly Lys Arg Ala Asp Gly Leu Lys Ala Lys Pro Leu
 20                  25                  30 aag cca tta gca gca aag caa ggg ctt caa gag aag aag gcc ctg agg       382
Lys Pro Leu Ala Ala Lys Gln Gly Leu Gln Glu Lys Lys Ala Leu Arg
35                  40                  45                  50 gat gta tcc aac att ggc aag ccc ccg gtg tct acg cgg aag ccc ctg       430
Asp Val Ser Asn Ile Gly Lys Pro Pro Val Ser Thr Arg Lys Pro Leu
                55                  60                  65 cag gac gtg tcc aac acc gcc aag ccc cga ggg cgc aac att tct gat       478
Gln Asp Val Ser Asn Thr Ala Lys Pro Arg Gly Arg Asn Ile Ser Asp
```

```
ggc act acc ttg aag aag act gct ctt cgc agc cat gag gcc acc aag      526
Gly Thr Thr Leu Lys Lys Thr Ala Leu Arg Ser His Glu Ala Thr Lys
            85                  90                  95 aac cca gtg aag aag act gta atc ttt tct gat gag acc gca aaa tgt      574
Asn Pro Val Lys Lys Thr Val Ile Phe Ser Asp Glu Thr Ala Lys Cys
    100                 105                 110 cat gaa tgg gct aag gat ggg gtg gag ggc acc cac ttc act ggg aat      622
His Glu Trp Ala Lys Asp Gly Val Glu Gly Thr His Phe Thr Gly Asn
115                 120                 125                 130 gat tct cag aag ttg gaa aag gac agt caa gac aaa cgt gtc aag aag      670
Asp Ser Gln Lys Leu Glu Lys Asp Ser Gln Asp Lys Arg Val Lys Lys
                135                 140                 145 aag gtg gag aaa ata atg tca gca ttg cac gac tgg cca gac gcg gta      718
Lys Val Glu Lys Ile Met Ser Ala Leu His Asp Trp Pro Asp Ala Val
            150                 155                 160 ttt gat cat gtg ctt ttt cca tct gag gtg gta gca gcg ttt ttt gaa      766
Phe Asp His Val Leu Phe Pro Ser Glu Val Val Ala Ala Phe Phe Glu
            165                 170                 175 gaa gta aaa gag atg gag ctg gaa cct gag att ctt cca gag aac aat      814
Glu Val Lys Glu Met Glu Leu Glu Pro Glu Ile Leu Pro Glu Asn Asn
180                 185                 190 agg cgt cgc tca agt tca ggt gat aaa atg aag ctg gct gaa gat cct      862
Arg Arg Arg Ser Ser Ser Gly Asp Lys Met Lys Leu Ala Glu Asp Pro
195                 200                 205                 210 ttc acg gaa gac gag ctt gac tac tac cca ttt ctt gag aac aat ccc      910
Phe Thr Glu Asp Glu Leu Asp Tyr Tyr Pro Phe Leu Glu Asn Asn Pro
                215                 220                 225 gtt gag ttt cag ctg aga gat gag cta cca ctc ctg gag cct gga atg      958
Val Glu Phe Gln Leu Arg Asp Glu Leu Pro Leu Leu Glu Pro Gly Met
            230                 235                 240 aac tga agaatgctaa tctgccccac ttgaaaagac ctcagaacag tgctattatc      1014
Asn atcattatcc tctttgcaaa ctctacttgc tcaggagcag tttatttgta gtagtagtag    1074
tagtaactag tatcctagat gttctgctgt atgtggttgg tgtgataatc attcacactt    1134
taggaagaac ccaagtagcg                                                 1154

<210> SEQ ID NO 2
<211> LENGTH: 243
<212> TYPE: PRT
<213> ORGANISM: Oryza sativa

<400> SEQUENCE: 2

Met Ala Ala Pro Thr Ala Thr Ala Val Phe Leu Asp Glu Asn Leu His
1               5                   10                  15

Ile His Arg Gly Pro Ala Gly Lys Arg Ala Asp Gly Leu Lys Ala Lys
            20                  25                  30

Pro Leu Lys Pro Leu Ala Ala Lys Gln Gly Leu Gln Glu Lys Lys Ala
        35                  40                  45

Leu Arg Asp Val Ser Asn Ile Gly Lys Pro Pro Val Ser Thr Arg Lys
    50                  55                  60

Pro Leu Gln Asp Val Ser Asn Thr Ala Lys Pro Arg Gly Arg Asn Ile
65                  70                  75                  80

Ser Asp Gly Thr Thr Leu Lys Lys Thr Ala Leu Arg Ser His Glu Ala
                85                  90                  95

Thr Lys Asn Pro Val Lys Lys Thr Val Ile Phe Ser Asp Glu Thr Ala
            100                 105                 110
```

```
Lys Cys His Glu Trp Ala Lys Asp Gly Val Glu Gly Thr His Phe Thr
            115                 120                 125

Gly Asn Asp Ser Gln Lys Leu Glu Lys Asp Ser Gln Asp Lys Arg Val
        130                 135                 140

Lys Lys Lys Val Glu Lys Ile Met Ser Ala Leu His Asp Trp Pro Asp
145                 150                 155                 160

Ala Val Phe Asp His Val Leu Phe Pro Ser Glu Val Val Ala Ala Phe
                165                 170                 175

Phe Glu Glu Val Lys Glu Met Glu Leu Glu Pro Glu Ile Leu Pro Glu
            180                 185                 190

Asn Asn Arg Arg Arg Ser Ser Ser Gly Asp Lys Met Lys Leu Ala Glu
            195                 200                 205

Asp Pro Phe Thr Glu Asp Glu Leu Asp Tyr Tyr Pro Phe Leu Glu Asn
        210                 215                 220

Asn Pro Val Glu Phe Gln Leu Arg Asp Glu Leu Pro Leu Leu Glu Pro
225                 230                 235                 240

Gly Met Asn

<210> SEQ ID NO 3
<211> LENGTH: 26
<212> TYPE: DNA
<213> ORGANISM: Artificial Sequence
<220> FEATURE:
<223> OTHER INFORMATION: Tos17-3911F primer

<400> SEQUENCE: 3
gagagcatca tcggttacat cttctc                                    26

<210> SEQ ID NO 4
<211> LENGTH: 24
<212> TYPE: DNA
<213> ORGANISM: Artificial Sequence
<220> FEATURE:
<223> OTHER INFORMATION: Tos17-xbaI-R

<400> SEQUENCE: 4
catgaaatag atccatgtat atct                                      24

<210> SEQ ID NO 5
<211> LENGTH: 20
<212> TYPE: DNA
<213> ORGANISM: Artificial Sequence
<220> FEATURE:
<223> OTHER INFORMATION: primer 0F

<400> SEQUENCE: 5
gccatcacaa atcagcaagc                                           20

<210> SEQ ID NO 6
<211> LENGTH: 21
<212> TYPE: DNA
<213> ORGANISM: Artificial Sequence
<220> FEATURE:
<223> OTHER INFORMATION: primer 3R

<400> SEQUENCE: 6
atggattgaa ggccaagcca c                                         21

<210> SEQ ID NO 7
<211> LENGTH: 20
<212> TYPE: DNA
```

```
<213> ORGANISM: Artificial Sequence
<220> FEATURE:
<223> OTHER INFORMATION: a primer used in probing for Tos17-inserted
      mutant

<400> SEQUENCE: 7
gtctggccag tcgtgcaatg                                                      20

<210> SEQ ID NO 8
<211> LENGTH: 20
<212> TYPE: DNA
<213> ORGANISM: Artificial Sequence
<220> FEATURE:
<223> OTHER INFORMATION: a primer used in probing for Tos17-inserted
      mutant

<400> SEQUENCE: 8
ctgctggcaa gagggctgat                                                      20

<210> SEQ ID NO 9
<211> LENGTH: 20
<212> TYPE: DNA
<213> ORGANISM: Artificial Sequence
<220> FEATURE:
<223> OTHER INFORMATION: a primer used in probing for Tos17-inserted
      mutant

<400> SEQUENCE: 9
tgggttcttg gtggcctcat                                                      20

<210> SEQ ID NO 10
<211> LENGTH: 20
<212> TYPE: DNA
<213> ORGANISM: Artificial Sequence
<220> FEATURE:
<223> OTHER INFORMATION: a primer used in probing for Tos17-inserted
      mutant

<400> SEQUENCE: 10
gccaagccac tgaagccatt                                                      20
```